US009406482B2

United States Patent
Mulders et al.

(10) Patent No.: US 9,406,482 B2
(45) Date of Patent: Aug. 2, 2016

(54) CHARGED-PARTICLE MICROSCOPE WITH RAMAN SPECTROSCOPY CAPABILITY

(71) Applicant: FEI Company, Hillsboro, OR (US)

(72) Inventors: Johannes Jacobus Lambertus Mulders, Eindhoven (NL); Laurens Kuipers, Amsterdam (NL)

(73) Assignee: FEI COMPANY, Hillsboro, OR (US)

( * ) Notice: Subject to any disclaimer, the term of this patent is extended or adjusted under 35 U.S.C. 154(b) by 0 days.

(21) Appl. No.: 14/326,341

(22) Filed: Jul. 8, 2014

(65) Prior Publication Data

US 2015/0009489 A1    Jan. 8, 2015

Related U.S. Application Data

(60) Provisional application No. 61/843,747, filed on Jul. 8, 2013.

(51) Int. Cl.
| | |
|---|---|
| *G01N 21/00* | (2006.01) |
| *H01J 37/26* | (2006.01) |
| *G01N 21/65* | (2006.01) |
| *H01J 37/22* | (2006.01) |
| *H01J 37/28* | (2006.01) |

(52) U.S. Cl.
CPC .............. *H01J 37/261* (2013.01); *G01N 21/65* (2013.01); *H01J 37/226* (2013.01); *H01J 37/28* (2013.01)

(58) Field of Classification Search
CPC .... H01J 37/32935; H01J 37/26; G01N 21/63; G01N 21/64; G01N 21/65; G01N 21/68; G01N 21/658; G01N 2015/1037; G01N 2021/656; G01J 3/02; G01J 3/44

USPC .............................................. 356/72–73, 301
See application file for complete search history.

(56) References Cited

U.S. PATENT DOCUMENTS

| 5,811,804 | A | | 9/1998 | Van Blitterswijk et al. |
|---|---|---|---|---|
| 6,118,123 | A | * | 9/2000 | Notoya .................... H01J 37/21 250/307 |

(Continued)

FOREIGN PATENT DOCUMENTS

| DE | 102009015341 | 10/2010 |
|---|---|---|
| JP | 2010190595 | 9/2010 |

OTHER PUBLICATIONS

Ammar, M.R., et al., "Characterization of graphite implanted with chlorine ions using combined Raman microspectometry and transmission electron microscopy on thin sections prepared by focused ion beam," Carbon, 2010, vol. 48, pp. 1244-1251.

*Primary Examiner* — Abdullahi Nur
(74) *Attorney, Agent, or Firm* — Scheinberg & Associates, PC; Michael O. Scheinberg; John E. Hillert (57) ABSTRACT

A charged-particle microscope with Raman spectroscopy capability and a method for examining a sample using a combined charged-particle microscope and Raman spectroscope. The method includes imaging a region of a sample by irradiating the sample with a beam of charged particles from the microscope; identifying a feature of interest in the region using the microscope; radiatively stimulating and spectroscopically analyzing a portion of the region comprising the feature of interest using a light spot of a width D from the spectroscope, wherein the feature of interest has at least one lateral dimension smaller than width D and, prior to using the light spot of the width D from the spectroscope, an in situ surface modification technique is used to cause positive discrimination of an expected Raman signal from the feature of interest relative to an expected Raman signal from the part of the portion other than the feature of interest.

20 Claims, 5 Drawing Sheets

(56) References Cited

U.S. PATENT DOCUMENTS

| | | |
|---|---|---|
| 6,654,118 B2 | 11/2003 | Bruce |
| 7,518,710 B2 | 4/2009 | Gao et al. |
| 7,532,314 B1 | 5/2009 | Black et al. |
| 7,993,585 B2 | 8/2011 | Black et al. |
| 8,598,542 B2 | 12/2013 | Toth et al. |
| 2014/0203191 A1 | 7/2014 | Buijsse et al. |
| 2014/0312226 A1* | 10/2014 | Boughorbel .......... H01J 37/222 250/307 |

* cited by examiner

CHARGED-PARTICLE MICROSCOPE WITH RAMAN SPECTROSCOPY CAPABILITY

This Application claims priority from U.S. Provisional Application 61/843,747, filed Jul. 8, 2013, which is hereby incorporated by reference.

The invention relates to a method of examining a sample using a combined charged-particle microscope and Raman spectroscope, whereby:

Said microscope irradiates a sample with a beam of charged particles so as to image a region of the sample;

Said spectroscope employs a light spot of width D to radiatively stimulate and spectroscopically analyze a portion of the sample, which method comprises the following steps:

Using the charged-particle microscope to identify a feature of interest in said region;

Choosing said portion that is analyzed by the Raman spectroscope to comprise this feature.

The invention also relates to a charged-particle microscope in which such a method can be performed.

As used throughout this text, the ensuing terms should be interpreted consistent with the following explanation:

The phrase "charged particle" encompasses an electron or ion (generally a positive ion, such as a Gallium ion or Helium ion, for example, although a negative ion is also possible; the ion in question may be a charged atom or molecule). The term may also refer to a proton, for example.

The term "microscope" refers to an apparatus that is used to create a magnified image of an object, feature or component that is generally too small to be seen in satisfactory detail with the naked human eye. In a charged-particle microscope (CPM), an imaging beam of charged particles is directed onto a sample using a so-called "particle-optical column", which comprises a collection of electrostatic and/or magnetic lenses that can be used to manipulate said beam, serving to provide it with a certain focus or deflection, for example, and/or to mitigate one or more aberrations therein.

The phrase "Raman spectroscope" (RS) refers to a device that exploits Raman scattering to spectroscopically investigate a sample, whereby an incoming beam of (monochromatic) light (which may be visible, but also infra-red or ultra-violet, for example) undergoes inelastic scattering in the sample. For more information on this topic, see, for example, the following Wikipedia links:
http://en.wikipedia.org/wiki/Raman_scattering
http://en.wikipedia.org/wiki/Raman_spectroscopy The concept of a "combined" CPM and RS as referred to here may, for example, encompass:

A CPM comprising an in situ RS module;

Separate CPM and RS apparatus that are connected to one another so as to have a shared sample holder.

In what follows, the invention will—by way of example—often be set forth in the specific context of electron microscopes. However, such simplification is intended solely for clarity/illustrative purposes, and should not be interpreted as limiting.

Electron microscopy is a well-known technique for imaging microscopic objects.

The basic genus of electron microscope has undergone evolution into a number of well-known apparatus species, such as the Transmission Electron Microscope (TEM), Scanning Electron Microscope (SEM), and Scanning Transmission Electron Microscope (STEM). In traditional electron microscopes, the imaging beam is "on" for an extended period of time during a given imaging session; however, electron microscopes are also available in which imaging occurs on the basis of a relatively short "flash" or "burst" of electrons, such an approach being of potential benefit when attempting to image moving samples or radiation-sensitive specimens, for example.

When a beam of particulate radiation (such as an electron beam or ion beam) impinges on a sample, it generally interacts with the sample in a manner that causes different types of emitted radiation to emanate from the sample. Such emitted radiation may, for example, comprise Secondary Electrons, Backscatter (BS) Electrons, visible/infrared/ultraviolet light (cathodoluminescence) and X-rays. Of these radiation types, electrons are relatively easy and cheap to detect, e.g. using a (solid-state or evacuated) photo-multiplier tube (PMT) in conjunction with a scintillator. The detection of said visible/infrared/ultraviolet light is also relatively straightforward, and can again be performed using a PMT (without scintillator) or a photodiode cell, for example. On the other hand, X-ray detectors generally tend to be relatively expensive and slow, but they are useful in performing compositional/elemental analyses of samples, such as in the case of so-called EDX (Energy Dispersive X-ray Spectroscopy) detectors, for example. In certain cases (such as in a TEM), the incoming beam of particulate radiation penetrates and re-emerges from the (thin) sample, and this re-emergent beam can be used for imaging purposes or to perform elemental analysis (e.g. using Electron Energy-Loss Spectroscopy (EELS)).

Although certain spectroscopic techniques (such as EDX and EELS) have been traditionally available in CPMs, these are generally of limited usefulness, e.g. because they do not give (sufficient) information as regards the molecular configuration in which detected elements are arranged. A far more useful/versatile spectroscopic technique is Raman spectroscopy, which probes a sample using a focused beam of optical radiation (light) rather than a charged-particle beam. Raman spectroscopy is relatively fast and accurate, and can provide very detailed information on parameters such as molecular composition, chirality, polymer chain length, crystalline structure, bond formation, etc. Analysis of samples using a combined CPM/RS thus allows users to acquire both shape/geometrical (and also some elemental) information (with the CPM) and compositional/chemical information (with the RS), and to combine these different types of information to achieve more comprehensive/useful results. For example, in the field of mineralogy/petrology, CPM analysis can yield information regarding (mineral/crystal) grain size, shape and location, and RS analysis can yield information concerning chemical composition/concentration and crystalline structure, allowing much more information to be extracted from (possibly precious/rare/costly/fragile) sample material.

However, although CPM and RS analysis complement each other in terms of the nature of the information that they provide, they also suffer from a substantial incompatibility. This has to do with the fact that both techniques use a different type of probing beam (charged particles vs. photons), with very different attainable lateral resolutions (of the order of nanometers vs. microns). This is not such a problem in fields such as mineralogy/petrology or the semiconductor industry, where structures being investigated (mineral/crystal grains or semiconductor devices, for example) are typically relative large—i.e. larger than the minimum attainable lateral resolution of either a CPM or RS. However, in other fields—such as nanotechnology, microbiology, molecular science, polymer science, catalysis science, pharmacology, etc.—structures of interest may be much smaller than the maximum attainable resolution with an RS, making it very difficult to extract meaningful RS information from such structures.

It is an object of the invention to address these issues. In particular, it is an object of the invention to provide a methodology whereby Raman spectroscopy can be more successfully combined with charged-particle microscopy, especially in the analysis of structures with sub-micron dimensions. More specifically, it is an object of the invention to provide a method that allows substantial improvement of the effective lateral resolution of Raman spectroscopy when used in combination with charged-particle microscopy.

These and other objects are achieved in a method as set forth in the opening paragraph, characterized in that:

Said feature has at least one lateral dimension smaller than D;

Prior to analysis of said feature using the Raman spectroscope, an in situ surface modification technique is used to cause positive discrimination of an expected Raman signal from said feature relative to an expected Raman signal from said portion other than said feature.

For purposes of clarity, it should be noted that the syntax "Raman signal" is here intended to refer to a detector signal produced by light that undergoes inelastic/Raman scattering at the sample in question; such a signal may comprise one or more Raman spectral lines. To qualify such a signal as "expected" is merely to label it as being a future occurrence, i.e. as being a signal that has yet to be obtained; the term "expected" does not necessarily imply that one has any prior knowledge/forecast of what said signal will look like. The surface modification technique is enacted upon the surface of the sample that "faces" the incoming charged-particle beam in the CPM, and that is to face the incoming optical beam of the RS. The phrase "positive discrimination" indicates relative enhancement, e.g. by strengthening and/or making more identifiable and/or filtering out unwanted "ancillary" signals, for instance.

In experiments leading to the invention, the inventors used a CPM to identify various relatively small structures of interest in a collection of samples, and then attempted to perform Raman spectroscopy on these features. However, a substantial problem was caused by the fact that many of the features concerned had lateral dimensions that were one or more orders of magnitude smaller than the size of the probing light spot produced on the sample by the employed RS, and, accordingly, were significantly smaller than the field of view of the RS. For example, assuming an RS spot size/field of view with a diameter D=1 μm, a feature with a characteristic dimension d=50 nm will occupy less than 1% of said field of view. Consequently, if a Raman spectrum is obtained from a portion of a sample comprising one such feature, then (in idealized terms):

Less than 1% of the Raman signal from said portion will be from the feature of interest, leading to a relatively poor signal-to-noise ratio;

More than 99% of said Raman signal will be from unknown, and essentially irrelevant, material.

Such a scenario can be worse than looking for a proverbial "needle in a haystack", because the haystack in such an instance will generally be a complete unknown, and the needle can also be (substantially) unknown. This effect can be so severe as to basically render any such RS analysis essentially useless. However, drawing from their experience in working with CPMs, the inventors realized that certain specialized techniques used in CPMs for completely unrelated purposes could be put to clever use in the field of Raman spectroscopy so as to "pre-manipulate" RS results towards greater specificity, accuracy and reliability. This was achieved by improving the effective lateral resolution of the employed RS through suitable pre-processing of the sample under investigation. In essence, the inventive approach seeks to cause positive discrimination of the (expected) Raman signal from a feature of interest relative to the (expected) Raman signal from the essentially uninteresting/irrelevant "landscape" surrounding/adjoining that feature. Such discrimination can be achieved via appropriate use of an in situ surface modification technique (SMT), as will be elucidated in more detail below.

In an embodiment of the present invention, said SMT is selected from the group comprising Electron Beam-Induced Deposition (EBID), Ion Beam-Induced Deposition (IBID), Electron Beam-Induced Etching (EBIE), Ion Beam-Induced Etching (IBIE), Focused Ion Beam (FIB) milling, and combinations hereof. These techniques can be briefly characterized as follows:

EBID and IBID are additive techniques, which can be used to deposit various materials onto a sample surface with a very high (lateral) spatial resolution (of the order of nanometers) and controllable thickness. A nozzle (or other dosing device) is used to administer a gas-phase precursor substance to said surface, where it undergoes a highly localized interaction with a focused electron beam (EDIB) or ion beam (IBID) in such a manner as to cause (ultimate) precipitation/deposition of solid material onto the surface in the zone of interaction. For more information, see, for example, the following Wikipedia link:

http://en.wikipedia.org.wiki/Electron_beam-induced_deposition

EBIE and IBIE are similar to EBID and IBID, respectively, except in that the localized interaction between the employed precursor substance and electron/ion beam in this case causes etching of the surface in the zone of interaction; these techniques are therefore subtractive rather than additive. To this end, one will generally employ a different precursor substance than in the case of EBID/IBID.

FIB milling is another subtractive technique, which can be used to cause localized ablation/sputtering of material from a sample surface, again with a very high (lateral) spatial resolution. Here, the material removal mechanism is essentially physical rather than chemical in nature. For more information, see, for example, the following Wikipedia link:

http://en.wikipedia.org/wiki/Focused_ion_beam

In all of these techniques, appropriately scanning/rastering the employed electron/ion beam over the surface of the sample will allow material to be deposited/removed according to a desired pattern. In addition, using plural passes over a given area will allow a greater depth of material to be deposited/removed in that area (as compared to a single pass). With reference to the terminology used above, and as will be set forth in greater detail below, these techniques can be used inter alia to achieve one or more of the following effects:

Amplification of the (expected) Raman signal from a feature of interest;

Attenuation of the (expected) Raman signal from the "landscape" in which said feature is located;

Conversion of the (expected) Raman signal from said "landscape" into a more recognizable (and, thus, more easily subtractable) signature (different to that from said feature of interest).

In a specific embodiment of the invention, the abovementioned positive discrimination is achieved by depositing a blanketing material on at least part of said portion other than said feature (i.e. on at least a part of said "landscape"), whereby said blanketing material is chosen so as to exhibit an effect selected from the group comprising:

Producing zero Raman signal;
Producing a relatively weak Raman signal;
Producing a known reference Raman signal, and combinations hereof. In this approach, one basically deposits an appropriately shaped "mask" that alters the perceived setting in which said feature is located. In a specific example, the employed blanketing material may comprise a distribution of platinum grains in a carbonaceous matrix that is deposited using EBID/IBID to a thickness of 100 nm, for instance. Such a blanketing layer will produce a known/reference Raman signal that differs from the Raman signal from said feature; suitable manipulation of the obtained spectrum (e.g. a subtraction/filtering operation) allows the spectrum of said feature to be derived from the combined Raman signal.

In a different embodiment of the invention, the aforementioned positive discrimination is caused by depositing an enhancing structure proximal said feature, which structure serves to amplify a Raman signal from said feature. Such a structure may take different forms, such as set forth in the following examples:

(i) A waveguide structure/nano-antenna adjacent to the feature, such as a so-called "bow-tie" structure. Such structures act as plasmonic resonance amplifiers. In the case of a bow-tie antenna, for example, opposing segments/wings of the bow-tie can be disposed so as to straddle the feature of interest. Such structures may, for example, comprise a (patterned/shaped) gold layer that is deposited (using EBID or IBID) from Au(CO)Cl precursor material (in which "CO" represents a carbonyl group, C=O)—although other layer materials, such as Ag or Pd, are also conceivable. In a specific example:

The thickness of such a patterned layer (which is easily defined/controlled) is of the order of about 50 nm;
It is used to create a bow-tie with lateral segment/wing dimensions of 60 nm (length)×20 nm (height) and having a central gap of width 15 nm between its segments/wings;
A feature of width d=13 nm is located in said gap. Note that, if the feature is wider than the gap size (i.e. d>15 nm in the current case), then amplification will only occur for the area of the feature within the gap. Ideally, the feature is exactly as wide as the gap.

(ii) A non-continuous "grid" can be deposited on top of the feature. Such a grid may, for example, comprise metallic grains/nano-dots of a given size and average spacing, whereby the size of the grains should be significantly lower than the wavelength of light used in the RS. The material of the grains should be such as to produce relatively low damping of plasmonic waves. Once again, gold (for example) may be used as a grid material, and can be deposited out of Au(CO)Cl precursor material using EDIB/IBID. By suitably choosing the flux (flow rate) of precursor material (from the nozzle that administers it), one can control the extent to which the deposition-triggering (electron or ion) beam scatters off of precursor molecules; in this way, one can deliberately increase primary beam scattering effects so as to naturally produce a granular structure in the deposited material (gold in the current example). Other candidate grid materials include Al, for instance. In a specific example:
The grain/nano-dot size is 3-15 nm;
The average spacing of the grains is 3-15 nm;
The flux of Au(CO)Cl precursor material used to produce such grains was $10^{14}$ molecules/cm$^2$ (at the sample surface), in combination with EBID at a beam current of 5 nA.
A grid as here alluded to essentially produces coupling of plasmonic waves in the spaces between the nano-dots.

(iii) One could also conceive a photonic amplifier structure, such as an optical resonance cavity, deposited proximal the feature of interest.

For more information on the deposition of gold nanostructures using Au(CO)Cl precursor material in conjunction with EBID, reference is made to the following journal article (by the inventors):

J. J. L. Mulders et al., J. Phys. D: Appl. Phys. 45 (2012), pp. 475301 et seq.

The previous two embodiments feature additive SMTs, but, if desired, the invention can also be performed using a subtractive SMT; in such an instance, the aforementioned positive discrimination is caused by removing material from said portion other than said feature (i.e. from at least part of said "landscape"). For example, FIB milling (or EBIE/IBIE) can be used to accurately remove material from around the feature of interest, so that the feature remains behind on a "pillar" that is surrounded by a "pit" in the sample surface. The depth of this pit is such that its bottom is essentially outside the focal reach of the probing RS beam, and its width is preferably as large as (or larger than) the diameter D of the RS field of view/light spot. In a specific example, the depth of such a pit may be of the order of about 2-3 μm, for instance (a depth that can typically be achieved in a matter of minutes using a technique such as FIB milling).

In an embodiment of the invention that may be regarded as involving a hybrid subtractive/additive technique, the SMT used to produce a pit as alluded to in the previous paragraph also causes inclusion/implantation of certain atomic/molecular species in the bottom of said pit. For example, FIB milling performed using Ga ions can leave a layer of Ga dopant in the pit bottom. In this way, even if the pit is not deep enough to fall outside the focal reach of the probing RS beam, its bottom will produce a Raman spectrum with an identifiable Ga signature, which can be subtracted from the total Raman spectrum to reveal the spectrum of the feature of interest.

As discussed above, the current invention provides a way in which to effectively improve the attainable resolution of Raman spectroscopy when performed on a sample that has been previously investigated using a CPM, whereby clever SMTs are used to allow an RS to "zoom in" on features that are well within the resolution capability of the CPM but below the nominal resolution capability of the RS. To facilitate co-usage of the CPM and RS in this manner, an embodiment of the current invention provides a sample under investigation with an alignment mark that can be detected by both the employed CPM and the RS. Such a mark should preferably have the following attributes:

It should have a shape/size that can be imaged by the CPM;
It should have a chemical signature that can be "recognized" by the RS.

According to the invention, the alignment mark in question can be provided using an SMT such as EBID/IBID, for example. In principle, one might also make such a mark using FIB milling, for example, whereby Ga ions (for instance) implanted in the sample by the FIB provide a chemical signature that can be recognized in the RS. The alignment mark is preferably relatively small, so as to maximize alignment accuracy, but it must be large enough to be satisfactorily detectable in the RS. Since the strength of a Raman signal will depend on the amount of material generating it, a mark that has relatively small lateral dimensions can still generate an acceptable Raman signal if it has a relatively large thickness (by way of compensation for its relatively small lateral area). In a specific example, the alignment mark is approximately the size of the field of view of the RS. It may, for example, have the shape of a cross or grating.

With reference to the subject matter of the previous paragraph, the skilled artisan will understand how to use such an alignment mark. For example, a combined CPM/RS according to the current invention can be provided with an optical position measuring system (comprising interferometers and/or encoders, for example) that allows the positional coordinates of a substrate holder (on which the substrate is mounted) to be determined relative to a (fixed) reference point (e.g. on a metrology frame). Using such a position measuring system, one can determine coordinates of a given feature of interest on the surface of a sample relative to a chosen alignment mark (e.g. by noting the coordinates of the mark and the coordinates of the feature, and then subtracting). If the sample is then moved from one "station" to another (e.g. from the CPM to the RS), a "capture scan" can be performed at the new station so as to locate said alignment mark; once this is located, said feature can be automatically located using the coordinates referred to above. An alignment/position measuring system of this type allows potential positioning errors—such as shift, skew and rotation errors—to be mitigated. As an alternative to an optical position measuring system, one could also conceive a position measuring system based on other principles, such as capacitance measurement, for example; the skilled artisan will be familiar with such possible alternatives.

The invention will now be elucidated in more detail on the basis of exemplary embodiments and the accompanying schematic drawings, in which.

In the Figures, where pertinent, corresponding parts are indicated using corresponding reference symbols.

Embodiment 1

Figure 1:
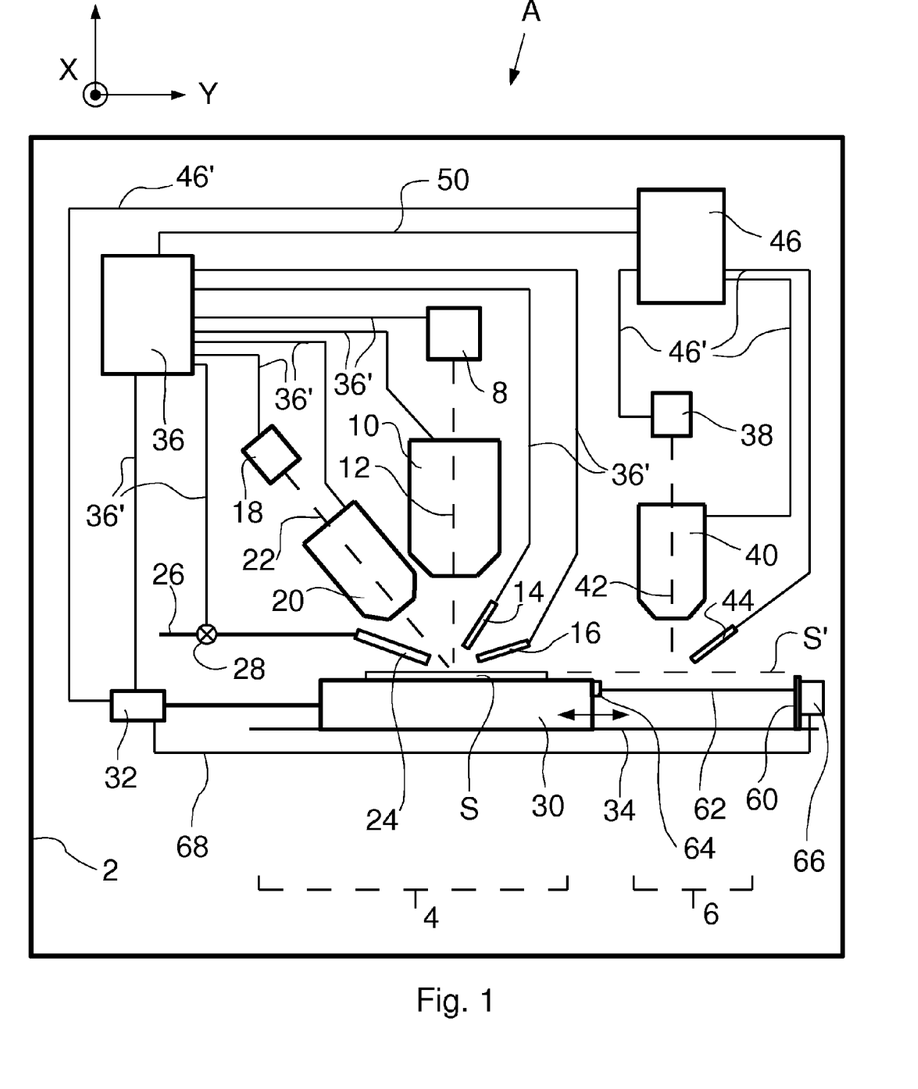
FIG. 1 renders an elevational view of an embodiment of an apparatus according to the current invention, in which an embodiment of a method according to the current invention can be performed.

FIG. 1 is a highly schematic depiction of an embodiment of an apparatus A according to the current invention, in which an embodiment of a method according to the current invention can be enacted. In the Figure, a charged-particle microscope (CPM) 4 and a Raman spectroscope (RS) 6 are both located in a shared vacuum enclosure 2, the RS 6 being disposed "off-axis" with respect to the CPM 4 (see below). The depicted CPM 4 is a so-called "FIB-SEM", as will be elucidated in more detail in what follows; however, this does not necessarily have to be the case, and the employed CPM 4 might instead comprise a TEM, for example. Moreover, the employed RS 6 could, in principle, be arranged so as to be "on-axis" with respect to the CPM 4. The skilled artisan will understand the various choices that can be made in these regards.

In the depicted CPM 4, an electron source 8 (such as a Schottky gun, for example) produces a beam of electrons that traverse a particle-optical column 10 that serves to focus them onto a chosen region of a substrate S. This particle-optical column 10 has a particle-optical axis 12, and will generally comprise a variety of electrostatic/magnetic lenses, deflectors, correctors (such as stigmators), etc. This focused electron beam will interact with the sample S in such a manner as to cause various types of "stimulated" radiation to be emitted from the sample S—including (for example) secondary electrons, backscattered electrons, X-rays and optical radiation (cathodoluminescence)—and one or more of these radiation types can be detected with the aid of detectors 14, 16. For example, detector 14 might be a combined scintillator/PMT, and detector 16 might be an EDX detector, for instance.

In addition to an electron-based functionality, the CPM 4 depicted here also has an ion-based functionality. To this end, an ion gun 18 produces a beam of ions (e.g. Ga ions) that traverse a particle-optical column 20 that serves to focus them onto the substrate S (within the field of view of the electron particle-optical column 10). This ion particle-optical column 20 has a particle-optical axis 22. The ion particle-optical column 20 can be used to perform ion-based imaging of the sample S (with the aid of detectors 14, 16, for example) and/or it can be used to perform ion-based surface modification techniques (SMTs) on the sample S, as will be explained below.

Also depicted in FIG. 1 is a gas administration nozzle 24 that is connected to a gas supply conduit 26 containing a valve/regulator 28; with the aid of these features 24, 26, 28 a suitable gas-phase precursor substance can be administered in a controlled manner to the vicinity of the point of intersection of the optical axes 12, 22, where it can interact with an electron beam travelling along axis 12 (to perform EBID/EBIE) and/or an ion beam travelling along axis 22 (to perform IBIB/IBIE) so as to cause highly localized deposition/etching at the exposed surface of the substrate S (depending on the type of precursor substance administered). Alternatively or supplementally, an ion beam travelling along axis 22 can be used to perform localized FIB milling of (and ion implantation in) the exposed surface of the substrate S, in which case a precursor substance does not necessarily have to be administered from nozzle 24.

The substrate S is held on a substrate holder 30 than can be positioned in multiple degrees of freedom by a positioning device (stage) 32. For example, the substrate holder 30 may comprise a chuck that can be moved smoothly in the XY plane (see the depicted Cartesian coordinate system), e.g. by sliding it over a flat reference surface 34 with the aid of an interposed bearing. Such movement allows different regions of the substrate S to be imaged and/or subjected to an SMT within the CPM 4. However, it also allows the substrate S to be moved to a location where it can be analyzed using the RS 6, as will be elucidated in more detail below.

Note that the CPM 4 is controlled by a controller (computer processor) 36, which is connected to various components of the CPM 4 via control lines (buses) 36'. This controller 36 can provide a variety of functions, such as synchronizing actions, providing setpoints, processing signals, performing calculations and displaying messages/information on a display device (not depicted), such as a flat panel display, for example.

As already alluded to above, the apparatus A includes an RS 6. This comprises a light source (e.g. laser) 38 that can be used to produce (non-ionizing) monochromatic light, e.g. with a wavelength λ of 514 nm or 785 nm, for instance. This light traverses an optical column 40 that serves to focus light from the source 38 onto a focal plane that is matched to the Z position of the substrate S (indicated here by dashed line S'). This optical column 40 has an optical axis 42, and will generally comprise a variety of lenses/mirrors, and possibly also other optical components, such as filters, polarizers, aperture plates, etc. Light focused by the optical column 40 will produce a light spot of diameter D on the exposed surface of the substrate S (see FIG. 2, for example), and light in this spot will undergo inelastic (Raman) scattering by irradiated molecules in the substrate S; as a result, the scattered light will contain (slightly shifted) wavelengths other than λ. The spectroscopic optical detector 44 can be used to collect (a portion of) this scattered light, and produce a Raman spectrum for the irradiated portion of the substrate S.

Note that the RS 6 is controlled by a controller (computer processor) 46, which is connected to various components of the RS 6 via control lines (buses) 46'. This controller 46 can provide a variety of functions, such as synchronizing actions, providing setpoints, processing signals, performing calculations and displaying messages/information on a display device (not depicted), such as a flat panel display, for example. The controller 46 is also connected to the controller 36 via a control line (bus) 50.

It should be noted that, unlike the CPM 4, the RS 6 does not necessarily have to be located in a vacuum environment in order to function properly. Accordingly, if one so desired, the RS 6 could be located outside the vacuum enclosure 2, and an airlock system (not depicted) could be used to allow the substrate holder 30 to shuttle back and forth between the CPM 4 and the RS 6. Alternatively, a transparent window could be located in the wall of the vacuum enclosure 2, so as to allow the RS 6 to optically access the inside of the vacuum enclosure 2. All such variants are examples of a "combined CPM and RS" as alluded to in the context of the current invention.

As already mentioned above, the RS 6 is disposed "off-axis" with respect to the CPM 4, in that the optical axis 42 of the RS 6 and the particle-optical axes 12, 22 of the CPM 4 do not have a common point of intersection. This particular configuration is chosen in this case so as to prevent excessive cluttering of the space around the sample S in the CPM 4; however, this does not necessarily have to be the case, and one could instead choose an "on-axis" configuration, whereby the CPM 4 and RS 6 both "look at" (i.e. are aligned toward) a common point.

Also schematically depicted in FIG. 1 is a position measuring system (PMS) with which the position of the substrate holder 30 can be measured. This PMS comprises a (laser) light source 60 that produces a (collimated) light beam 62 that is directed at the substrate holder 30. A reflective element 64 (e.g. interferometer retroflector or reflective encoder scale) that is mounted on the substrate holder 30 reflects the beam 62 back to a detector 66, which is fixed to a reference frame (not depicted). From analysis of the reflected beam, the detector 66 can determine the (momentary) position of the substrate holder 30, and share this information (in a feedback loop) with the positioning device 32 via control line (bus) 68. Items 62,64,66,68 collectively form a measurement "branch", which serves to measure position along a single direction/axis (e.g. Y position if branch 60,62,64,66 is interferometry-based, or X position if it is encoder-based). Although only one such branch is depicted here, a typical PMS will contain a plurality of such branches along complementary axes, so as to be able to measure position in plural coordinates (e.g. Y and X).

The CPM 4 and RS 6 will each have an alignment functionality, by means of which they can locate an alignment mark on the substrate S (and also possibly on the substrate holder 30). This alignment functionality works together with the PMS described in the previous paragraph to allow the position of features on the substrate S to be determined relative to a reference that can be used by both the CPM 4 and the RS 6. The skilled artisan will be very familiar with the structure and operation of such alignment systems, which need not be discussed here in greater detail. In accordance with the present invention, the substrate S may be provided on its topside with an alignment mark (not depicted) that can be imaged ("seen") by CPM 4 and that can be chemically detected ("sniffed out") by RS 6—thus allowing such a mark to be jointly utilized by both the CPM 4 and the RS 6.

The skilled artisan will understand that, if the CPM 4 comprised a TEM rather than a SEM, then (inter alia):

The substrate holder 30 would be embodied differently, so as to allow electrons from the particle-optical column 10 to pass unhindered through the sample S (e.g. by gripping the sides of the sample);

One or more detectors (and/or just a simple fluorescent screen) would be located "downstream" of the sample S along (an extension of) the particle-optical axis 12.

The skilled artisan will also understand that the interior of the enclosure 2 does not have to be kept at a strict vacuum; for example, in a so-called "Environmental SEM", a background atmosphere of a given gas is deliberately introduced/maintained within the enclosure 2.

Having described an embodiment of an apparatus according to the current invention, examples will now be given of manners in which such an apparatus can be used to perform embodiments of methods according to the present invention.

Embodiment 2

Figure 2:
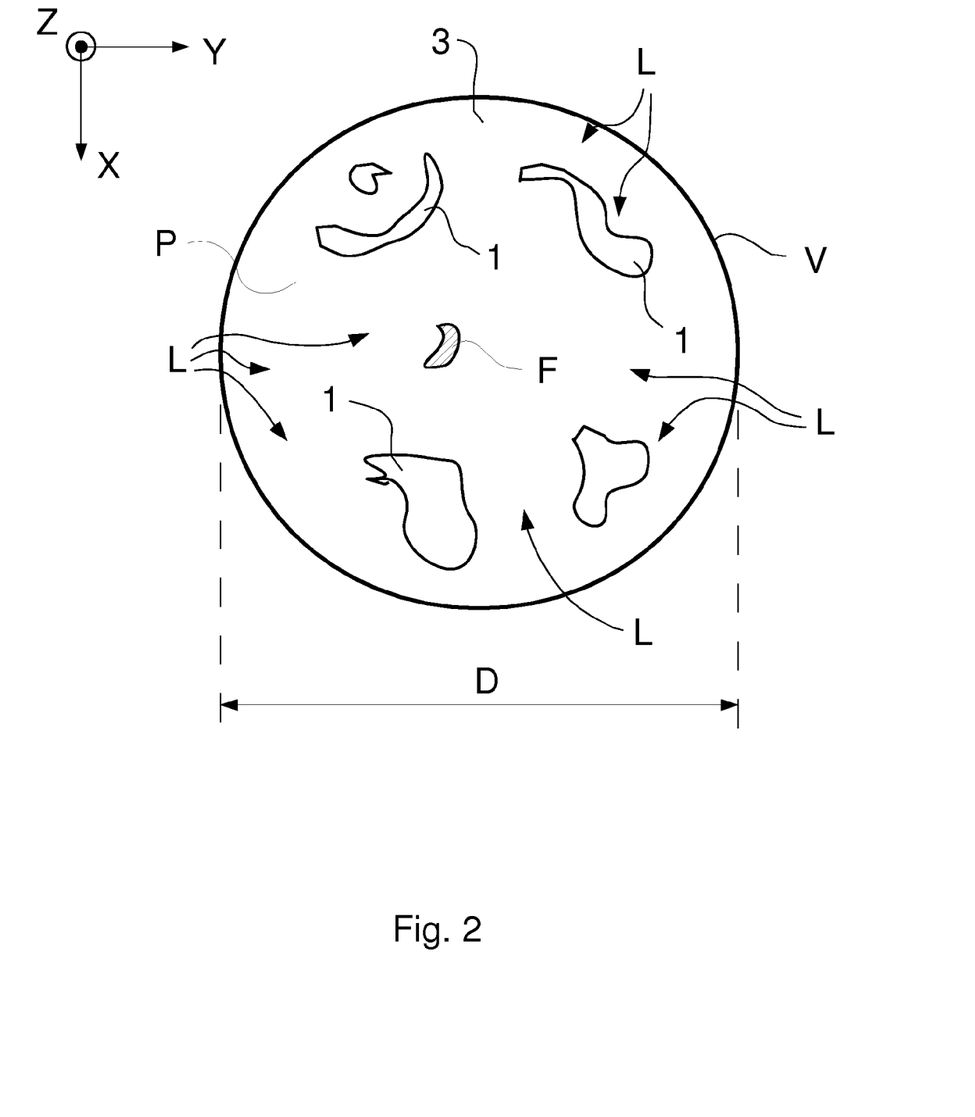
FIG. 2 renders a plan view of an aspect of part of the apparatus of FIG. 1 when in use, more particularly a field of view of the Raman Spectroscope of FIG. 1.

FIG. 2 renders a plan view of an aspect of part of the apparatus A of FIG. 1 when in use, more particularly a (schematic) field of view V of the RS 6 of FIG. 1. In this particular case, the field of view V is a circle of diameter D. Within this field of view V, a portion P of the sample S is visible, comprising various features 1 that can be identified against a "background" 3. For example:

The features 1 might be parts of a biological cell, and the background 3 might be a body of cell fluid;

The features 1 might be grains of a particular mineral type, and the background 3 might a rock matrix in which they are embedded;

The features 1 might be contaminant/dopant bodies in a mass 3 of semiconductor material, etc.

As is evident from the Figure, some of the features 1 (in this particular case, all of them) have lateral dimensions (in the XY plane) that are (much) smaller than D. In a particular example, D is of the order of about 1 μm and the features 1 have (exemplary) lateral dimensions ranging from about 20 nm to about 200 nm. Such feature sizes can be easily resolved using the CPM 4 of FIG. 1 and, in a prior investigation of the sample S using that CPM 4, a particular feature F amongst the features 1 has been identified as being of interest. However, although the CPM 4 can provide good information regarding the shape/geometry of feature F, and also some information regarding its composition (via EDX, for example), more detailed compositional information regarding the feature F is desired, e.g. via a Raman spectrum obtained using the RS 6.

Unfortunately, one is now confronted with the substantial difference in resolution between the CPM 4 and RS 6, and this causes a considerable problem in that the RS 6 will look at all light scattered from the field of view V—regardless of what part of the field of view V it comes from. Scattered light from all features 1 and the background 3 (within the field of view V) will be mixed with scattered light emanating from feature F, and the resulting Raman spectrum will be a "jumble" of spectral lines from all these sources. In other words, spectral information from feature F will only be obtained as an (unknown) component of a convoluted spectrum from the whole field of view V. This obviously greatly limits the usefulness of Raman spectroscopy in this case.

The current invention addresses this problem by using in situ SMTs to prepare the sample S after investigation by the CPM 4 and prior to analysis by the RS 6, in such a manner as to cause positive discrimination of an expected Raman signal from feature F relative to an expected Raman signal from the rest of the field of view V excluding F, i.e. from the "landscape" L surrounding F (in the current example, this landscape L comprises the background 3 and all features 1 other than F). Examples of the inventive method using different SMTs will now be given.

Embodiment 3

Figure 3:
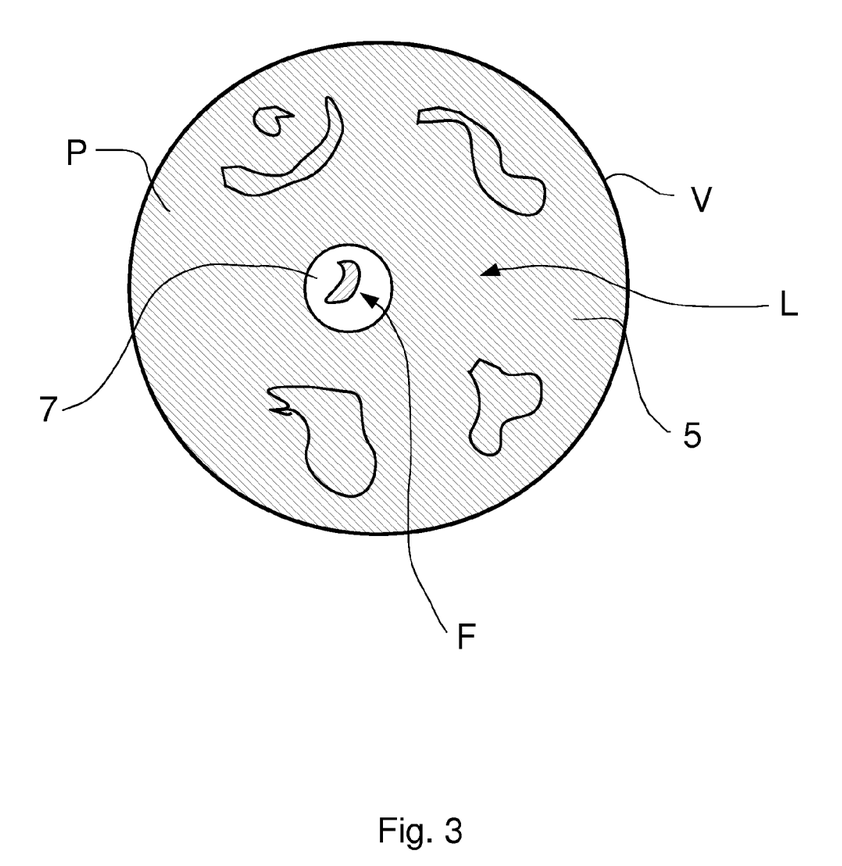
FIG. 3 shows the subject of FIG. 2 after performance of a particular surface modification technique prior to obtaining a Raman spectrum, according to a particular embodiment of the current invention.

In FIG. 3, a "mask" 5 of blanketing material (such as Au, Al or Ag) has been deposited on the sample S so as to cover the landscape L in the field of view V with the exception of a small exclusion zone 7 around the feature F. Here, the exclusion zone 7 is schematically depicted as being a relatively "roomy" circle around the feature F but, if so desired, it may take other shapes, and, in particular, may be more tightly fitted/matched to the outline of feature F. The mask 5 can be deposited using a technique such as EBID or IBID at the CPM 4 in FIG. 1, for instance (as set forth above). A Raman spectrum of the field of view V in this case will be the sum of:
  (i) The (unknown) Raman spectrum from the inside of exclusion zone 7;
  (ii) The (known) Raman spectrum from the blanketing material of mask 5.

The spectrum (ii) may be:
  Zero (or very weak) if the blanketing material is a strong absorber of the employed light from source 38, or comprises a material that does not demonstrate strong Raman scattering. Examples of such latter materials include pure metals, such as Au, Al and/or Ag, for instance; or
  An easily recognizable reference spectrum, such as in the case of a mask 5 comprising small Pt grains in a carboneous matrix, for instance.

In either case, the effect of using the mask 5 is essentially to "replace" the unknown landscape L by a controlled neighborhood 5, thus effectively narrowing the resolution of the RS 6 down to the size of the exclusion zone 7. One can then distinguish the following two cases:
  If the exclusion zone 7 is well fitted/matched to the contours of feature F, then spectrum (i) will correspond to the sought-after spectrum of feature F.
  If the exclusion zone 7 is a relatively "loose fit" around feature F—so that it also encompasses a small piece of background 3—then spectrum (i) will be the sum of the Raman spectrum from feature F plus a small piece of background 3. If the composition of background 3 within exclusion zone 7 is known (or can be guessed), then the Raman spectrum of feature F can be distilled from spectrum (i) by subtracting the (known/guessed) Raman contribution from said small piece of background 3.

The embodiment just presented was one in which positive discrimination of the Raman signal from feature F relative to landscape L (according to the invention) was achieved by suppressing/standardizing the Raman spectrum from landscape L whilst essentially leaving feature F as it was. An example will now be given in which an opposite approach is taken, namely amplification of the signal from feature F whilst leaving landscape L essentially as it is. Such amplification is achieved by depositing a suitable enhancing structure proximal the feature F.

Embodiment 4

Figure 4:
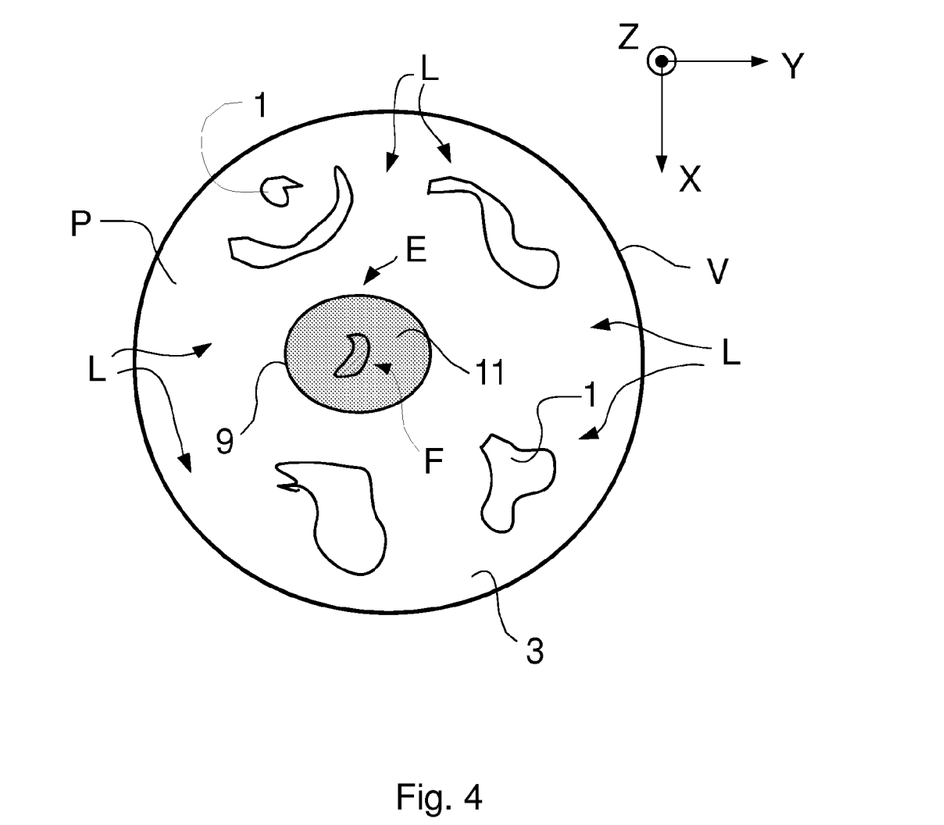
FIG. 4 shows the subject of FIG. 2 after performance of a different surface modification technique prior to obtaining a Raman spectrum, according to a different embodiment of the current invention.

In FIG. 4, the enhancing structure E alluded to above takes the form of a localized "patch" 9 comprising a non-continuous layer 11 of (metallic) material, which patch 9 is disposed on top of the feature F (i.e. so as to overlie it along the Z direction). The term "non-continuous" here refers to a layer that is not fully "closed", but instead comprises distributed openings, e.g. as in the case of a grid structure. An example of such a grid is an array of metallic (e.g. Au, Ag or Al) nano-dots of size ca. 10 nm and at an average spacing of 10-100 nm, which may be deposited from a precursor material such as Au(CO)Cl or $Me_2AuAcAc$ (dimethyl gold acetylacetate), for example (using the EBID/IBID functionality of CPM 4 in FIG. 1, for instance). In the current illustration, the patch 9 is schematically depicted as being a relatively "roomy" ellipse around the feature F but, if so desired, it may take other shapes, and, in particular, may be more tightly fitted/matched to the outline of feature F (so as to overlay less of the background 3).

As explained above, such a structure E can serve to significantly amplify the Raman signal from feature F (and any piece of the background 3 underneath the patch 9), e.g. by a factor of as much as 100-10,000. In this way, the Raman spectrum from feature F is augmented to such an extent that it effectively "drowns out" the (unknown) Raman spectrum from landscape L. Analogous to the situation in Embodiment 3:
  If the patch 9 is well fitted/matched to the contours of feature F, then the spectrum from patch 9 ("patch spectrum") will correspond to the sought-after spectrum of feature F.
  If the patch 9 is a relatively "loose fit" around feature F—so that it also encompasses a small piece of background 3—then said patch spectrum will be the sum of the Raman spectrum from feature F plus a small piece of background 3. If the composition of background 3 beneath patch 9 is known (or can be guessed), then the Raman spectrum of feature F can be distilled from said patch spectrum by subtracting the (known/guessed) Raman contribution from said small piece of background 3.

This embodiment effectively represents a form of localized Surface-Enhanced Raman Spectroscopy (SERS), whereby pertinent surface enhancement is confined to the feature of interest (and its immediate vicinity).

Embodiment 5

Figure 5:
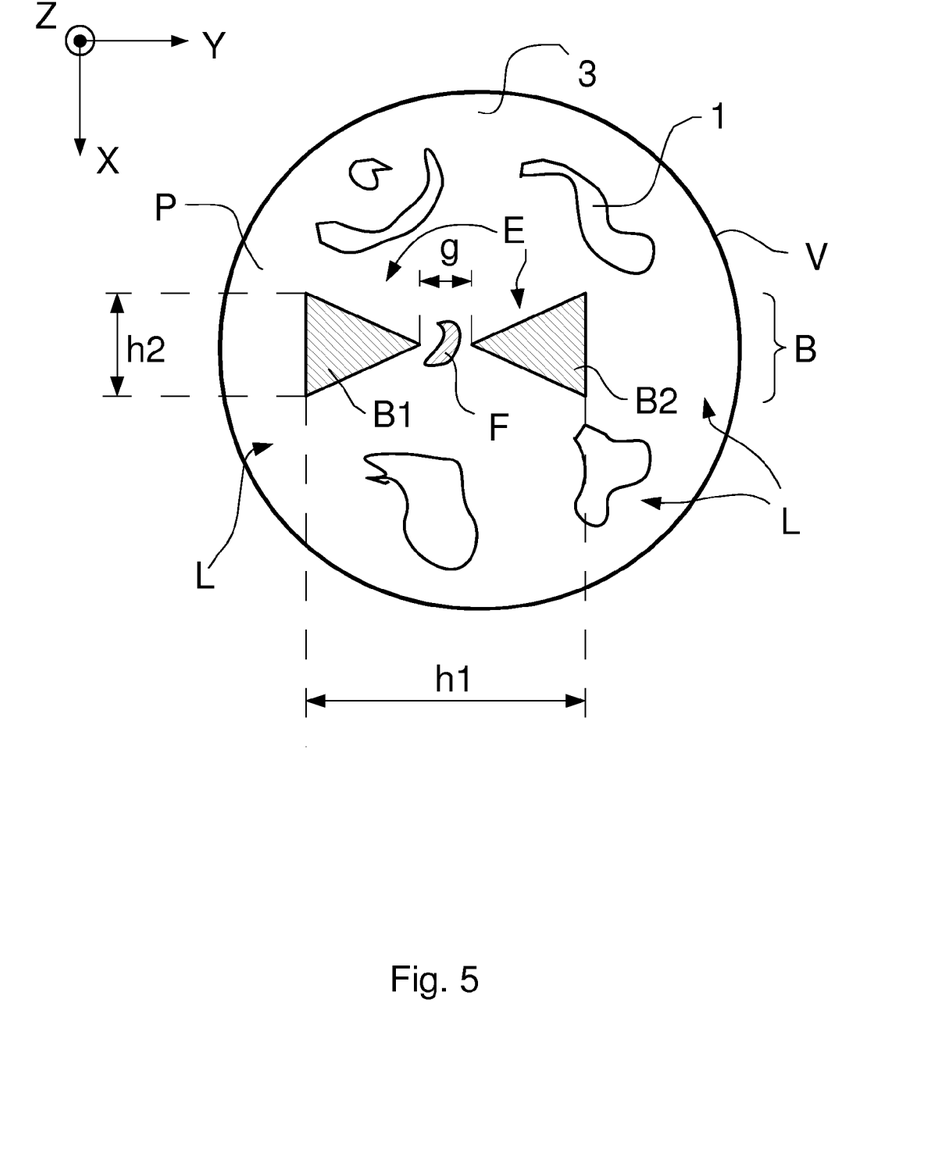
FIG. 5 shows the subject of FIG. 2 after performance of another surface modification technique prior to obtaining a Raman spectrum, according to another embodiment of the current invention.

FIG. 5 depicts an alternative enhancing structure E, which now takes the form of a so-called "bow-tie" antenna B, having two (substantially triangular) segments/wings B1, B2 that are symmetrically positioned so as to straddle feature F. The bow-tie B acts as a nano-antenna that substantially amplifies the Raman spectrum from feature F via plasmonic resonance effects. As here depicted, the bow-tie B has a length $d_1=135$ nm (parallel to Y) and a height $d_2=20$ nm (parallel to X), with a gap of width $g=15$ nm (parallel to Y) between the segments/wings B1, B2 and a film thickness of 50 nm (along the Z direction). In the current case, the bow-tie B is aligned along the Y direction, but this does not necessarily have to be the case, and it can also have other orientations in the XY plane. The segments/wings B1, B2 are comprised of a metal such as Au, for example, and were deposited at the desired/required location with respect to feature F using the EBID and/or IBID functionality at CPM 4 in FIG. 1, for instance.

We claim as follows:

1. A method of examining a sample using a combined charged-particle microscope and Raman spectroscope, whereby:
    said microscope irradiates a sample with a beam of charged particles so as to image a region of the sample;
    said spectroscope employs a light spot of width D to radiatively stimulate and spectroscopically analyze a portion of the sample,
    which method comprises the following steps:
    using the charged-particle microscope to identify a feature of interest in said region;
    choosing said portion that is analyzed by the Raman spectroscope to comprise this feature,
    wherein:
    said feature has at least one lateral dimension smaller than D;
    Prior to analysis of said feature using the Raman spectroscope, an in situ surface modification technique is used to cause positive discrimination of an expected Raman signal from said feature relative to an expected Raman signal from said portion other than feature.

2. A method according to claim 1, wherein said surface modification technique is selected from the group comprising Electron Beam-Induced Deposition, Ion Beam-Induced Deposition, Electron Beam-Induced Etching, Ion Beam-Induced Etching, Focused Ion Beam milling, and combinations hereof.

3. A method according to claim 1, wherein said discrimination is caused by depositing a blanketing material on at least part of said portion other than said feature, whereby said blanketing material is chosen so as to exhibit an effect selected from the group comprising:
    producing zero Raman signal;
    producing a relatively weak Raman signal;
    producing a known reference Raman signal,
    and combinations hereof.

4. A method according to claim 1, wherein said discrimination is caused by depositing an enhancing structure proximal said feature, which structure serves to amplify a Raman signal from said feature.

5. A method according to claim 4, wherein said enhancing structure is selected from the group comprising:
    a plasmonic amplifier structure provided adjacent to said feature;
    a non-continuous grid structure provided on top of said feature; and
    a photonic amplifier structure provided proximal said feature;
    and combinations hereof.

6. The method according to claim 1, wherein said discrimination is caused by removing material from said portion other than said feature.

7. A method according to claim 1, wherein said sample is provided with an alignment mark that can be imaged in said microscope and can be chemically detected in said Raman spectroscope.

8. A charged-particle microscope, comprising:
    a sample holder for holding a sample;
    a particle-optical column for directing at least one beam of particulate radiation onto a surface of the sample;
    a first detector for detecting radiation emerging from the sample as a result of irradiation by said beam of particulate radiation;
    a Raman spectroscopy module comprising:
        an optical column for directing a light spot onto the sample, and
        a second detector for detecting light that is inelastically scattered in said light spot; and
        at least one apparatus for performing a surface modification technique upon the sample, which technique comprises at least one of the following actions:
        localized addition of material to the sample; or
        localized removal of material from the sample,
    wherein the charged-particle microscope is configured to:
        image the sample by directing the at least one beam of particular radiation onto the surface of the sample;
        acquire compositional/chemical information using the Raman spectroscopy module.

9. A charged-particle microscope according to claim 8, wherein said surface modification technique is selected from the group comprising:
    Electron Beam-Induced Deposition;
    Ion Beam-Induced Deposition;
    Electron Beam-Induced Etching;
    Ion Beam-Induced Etching;
    Focused Ion Beam milling,
    and combinations hereof.

10. The charged-particle microscope of claim 8, wherein the at least one apparatus comprises an ion particle-optical column.

11. The charged-particle microscope of claim 10, wherein the ion particle-optical column and the particle-optical column for directing at least one beam of particulate radiation onto a surface of the sample are the same.

12. The charged-particle microscope of claim 8, wherein the particle-optical column comprises an electron source configured to produce a beam of electrons that traverses the particle-optical column.

13. The charged-particle microscope of claim 12, wherein the at least one apparatus and the particle-optical column for directing at least one beam of particulate radiation onto a surface of the sample are the same.

14. The charged-particle microscope of claim 8, wherein the apparatus is configured to deposit, using the surface modification technique, a mask of blanketing material on a surface of the sample within a field of view of the optical column of the Raman spectroscopy module and surrounding a feature of interest of the sample.

15. The charged-particle microscope of claim 14, wherein the surface modification technique comprises an electron beam-induced deposition, an ion beam-induced deposition, or a combination thereof.

16. The charged particle microscope of claim 8, wherein the apparatus is configured to form, using the surface modification technique, an array of metallic nano-dots on top of a feature of interest of the sample and within a field of view of the optical column of the Raman spectroscopy module.

17. The charged-particle microscope of claim 16, wherein the surface modification technique comprises an electron beam-induced deposition, an ion beam-induced deposition, or a combination thereof.

18. The charged particle microscope of claim 8, wherein the apparatus is configured to deposit, using the surface modification technique, a bow-tie antenna having two substantially triangular segments symmetrically positioned so as to straddle a feature of interest of the sample within a field of view of the optical column of the Raman spectroscopy module.

19. The charged-particle microscope of claim 18, wherein the surface modification technique comprises an electron beam-induced deposition, an ion beam-induced deposition, or a combination thereof.

20. A method of examining a sample using a combined charged-particle microscope and Raman spectroscope, comprising:
- imaging a region of a sample by irradiating the sample with a beam of charged particles from said charged-particle microscope;
- identifying a feature of interest in the region using the charged-particle microscope;
- radiatively stimulating and spectroscopically analyzing a portion of the region comprising the feature of interest using a light spot of a width D from the Raman spectroscope,
- wherein said feature of interest has at least one lateral dimension smaller than width D and, prior to using the light spot of the width D from the Raman spectroscope, an in situ surface modification technique is used to cause positive discrimination of an expected Raman signal from said feature of interest relative to an expected Raman signal from the part of the portion other than the feature of interest.

* * * * *